United States Patent [19]

Herman

[11] 4,069,968
[45] Jan. 24, 1978

[54] DISPOSABLE TUBING HARNESS FOR USE WITH BLOOD WASHING APPARATUS

[75] Inventor: Wallace Unto Herman, Stamford, Conn.

[73] Assignee: Union Carbide Corporation, New York, N.Y.

[21] Appl. No.: 737,607

[22] Filed: Nov. 1, 1976

[51] Int. Cl.² .............................................. B04B 15/02
[52] U.S. Cl. .................................................. 233/14 R
[58] Field of Search ..................... 233/1 R, 1 D, 14 R, 233/14 A, 3, 19 R; 211/71; 128/272, 214 D, 2 F, 210/416

[56] References Cited

U.S. PATENT DOCUMENTS

| 3,452,924 | 7/1969 | Schultz | 233/14 R |
|---|---|---|---|
| 3,489,145 | 1/1970 | Judson et al. | 233/19 R |
| 3,634,228 | 1/1972 | Latham | 233/14 R |
| 3,877,634 | 4/1975 | Rohde et al. | 233/14 R |
| 3,987,961 | 10/1976 | Sinn et al. | 233/14 R |

Primary Examiner—George H. Krizmanich
Attorney, Agent, or Firm—Frederick J. McCarthy, Jr.

[57] ABSTRACT

Disposable flexible tubing harness for use with a blood washing device providing connections between packages for containing liquids and the blood washing device.

2 Claims, 7 Drawing Figures

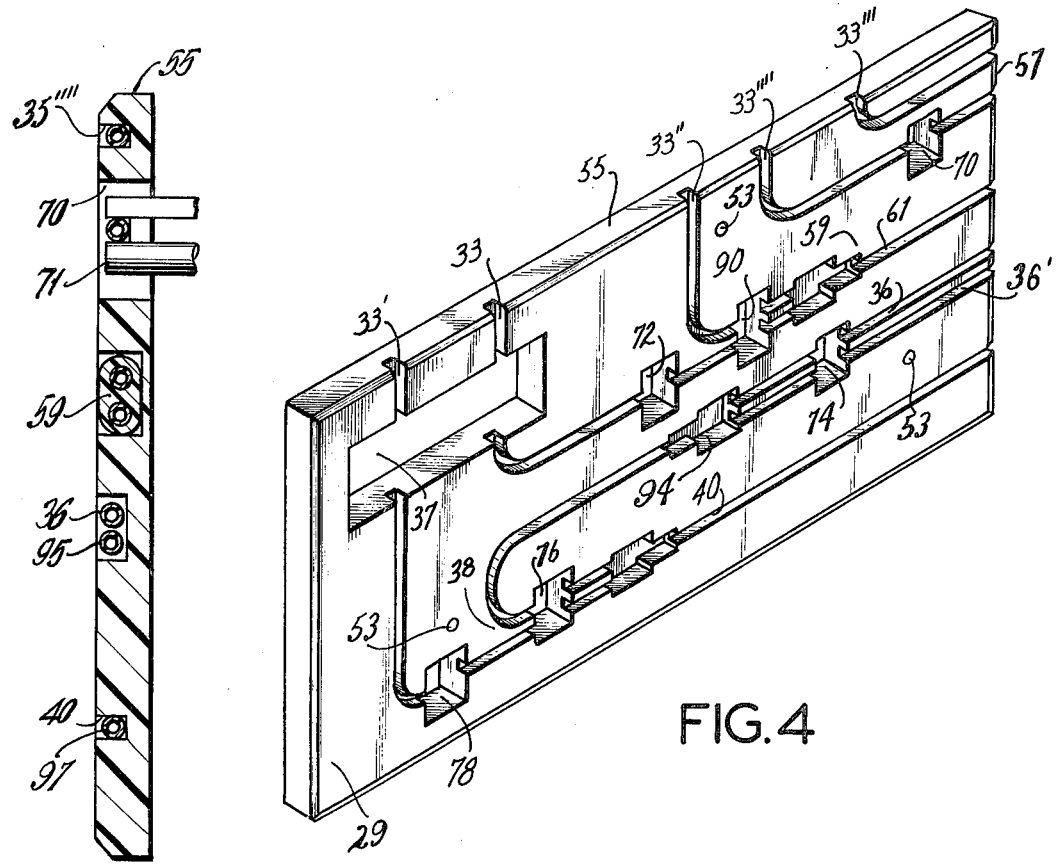
FIG.3
FIG.4
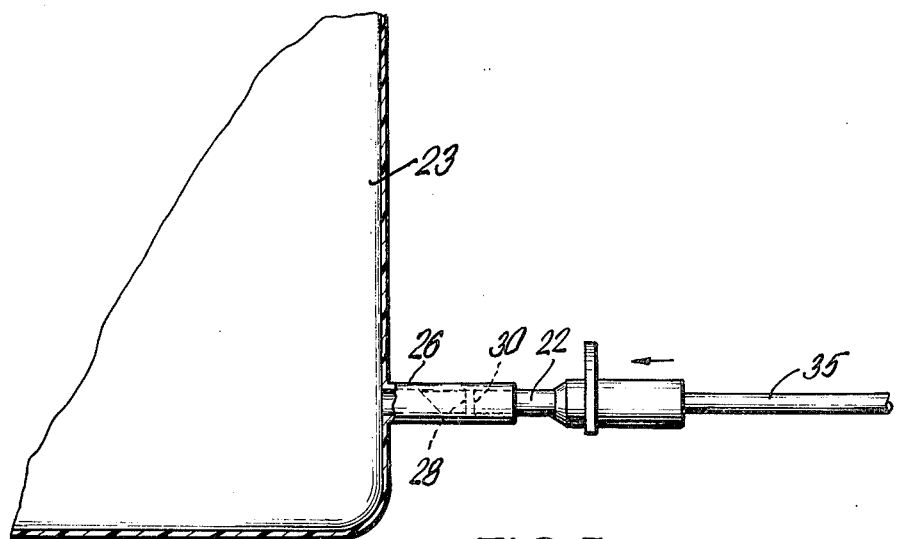
FIG.5

DISPOSABLE TUBING HARNESS FOR USE WITH BLOOD WASHING APPARATUS

The present invention relates to blood washing apparatus and more particularly to a disposable tubing arrangement or harness for use with a blood washing apparatus.

Blood washing is a procedure known to the art, for example, as described in U.S. Pat. No. 3,982,691 — Centrifuge Separation and Washing Device and Method — Charles A. Schutz issued Sept. 28, 1976. As described in the above-noted U.S. Patent human blood from volunteer donors is washed to remove unwanted constituents such as contaminants, toxicants, viruses, medicants, glycerines, cellular debris and the like, using a device based on centrifugal separation. Such a device includes a rotatable enclosure into which liquids, such as blood and wash liquids, e.g., saline solutions are injected, and from which the washed blood, wash liquids and unwanted constituents are removed. While the device described in the above-noted patent can be used to wash blood continuously, in a particular mode of operation, a predetermined amount of blood e.g., a package available from a blood banking organization, is washed using predetermined packaged quantities of wash solution. Under such circumstances it is desirable to provide a disposable connection between the packages of blood and wash liquids and the blood washing device, and between the blood washing device and liquid collection packages.

It is therefore an object of the present invention to provide a disposable tubing harness connection between a blood washing device and packaged liquids and liquid collection packages.

Other objects will be apparent from the following description and claims taken in conjunction with the drawing wherein FIG. 1 shows somewhat schematically a blood washing device which is provided with a disposable tubing harness arrangement in accordance with the present invention, FIGS. 2, 2(a) and 2(b) show in more detail the disposable tubing harness arrangement in accordance with the present invention, FIG. 3 is a section through 3—3 of FIG. 2

FIG. 4 shows the harness support member of FIG. 2 without tubing and

FIG. 5 shows a technique for connecting liquid containing packages to the tubes of the harness arrangement of the present invention.

Figure 1:
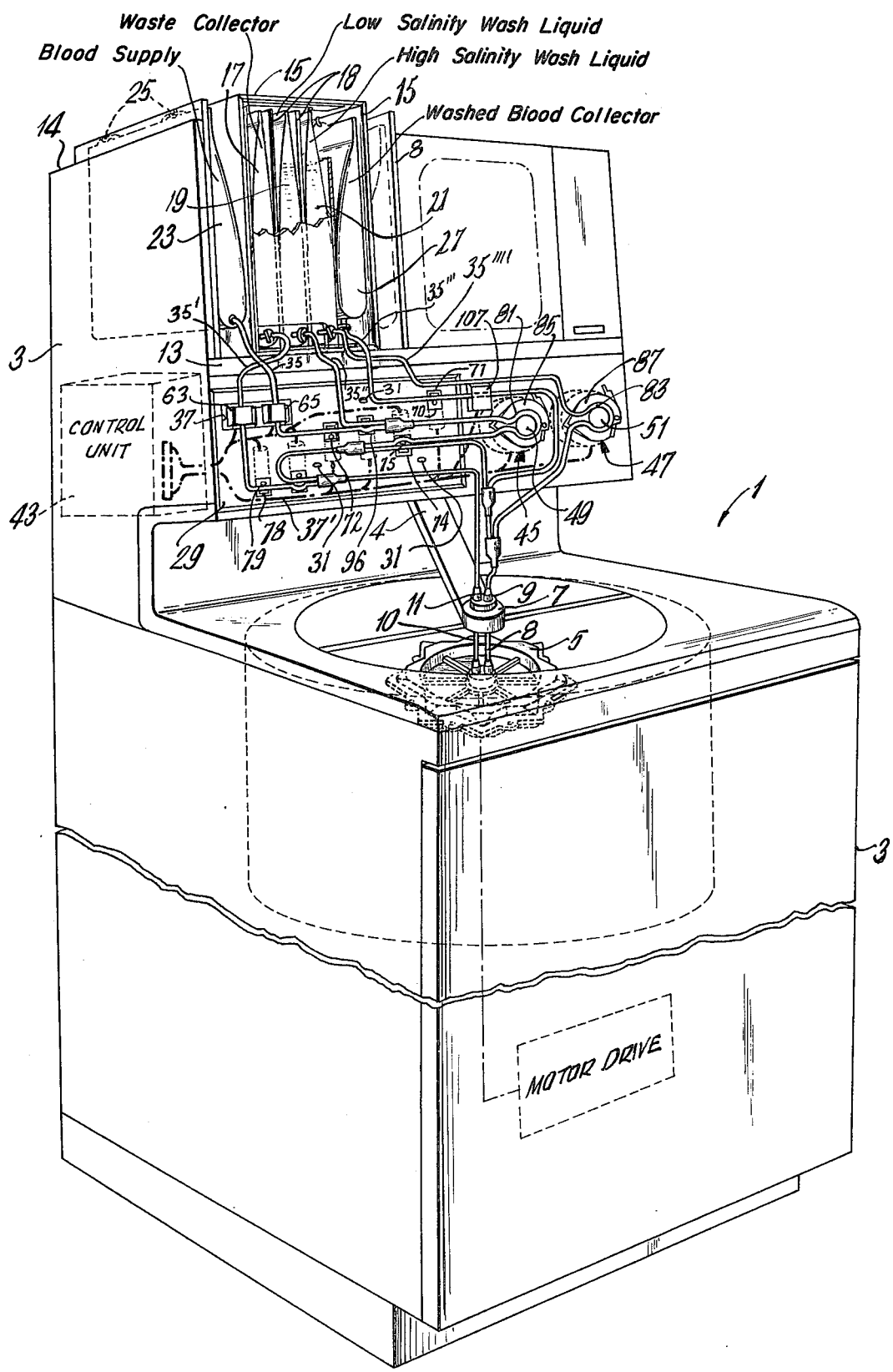

With reference to FIG. 1 of the drawing, a blood washing apparatus is indicated at 1 having an enclosing housing 3 in which is contained a rotatable enclosure means 5 such as the type described in the above-noted U.S. Pat. No. 3,982,691 which washes blood cells in the manner described in the patent.

A fluid connector 7, supported on arm 4 above entry conduit 8 and exit conduit 10 provides fluid communication with blood washing enclosure means 5. Fluid connector 7 has two conduits 9 and 11 for the entry and removal of liquid as hereinafter described.

Housing member 3 is provided with a shelf member 13 and side supports 14 and 8 which supports a container 15, having partitions 18, e.g. made of cardboard, which supportably holds an initially empty waste package 17, a low concentration saline solution containing package 19, and a high concentration saline solution containing package 21. A blood containing package 23, such as a package obtained from a blood bank, is supported by means of hooks on side support 14 as indicated at 25.

A washed blood collection package 27, initially arranged in container 15, is similarly supported on side support 8 during blood washing. The above-described packages 17, 19, 21, 23 and 27 are suitably made of a transparent flexible plastic material such as polyolefins and the like.

The horizontally disposed array of adjacent packages 17, 19, 21, 23 and 27 are located above a board-like member 29 which is removably engaged to housing 3 by support pins as indicated at 31. Board-like member 29 is suitably made of polyvinyl chloride and contains grooves 33, 33', etc., as particularly indicated in FIG. 2 and 4 which respectively engage and securely hold flexible tubes 35, 35', etc., which are transparent and also suitably made of polyvinyl and the like. Board like member 29 also has openings as hereinafter described to provide clearance for valves and sensors which are mounted on housing 3 and which receive electrical signals from or provide electrical signals to a conventional electrical control unit 43 which is contained within housing 3. Housing 3 also contains conventional peristaltic pumps 45 and 47 which have motor driven shaft extensions 49 and 51 respectively which have cross-sections lying in substantially the same vertical plane as the grooves 33, 33', etc., of board-like member 29. The rotation of the shafts 49 and 51 of pumps 45 and 47 may be controlled by signals from control unit 43.

Figure 2:
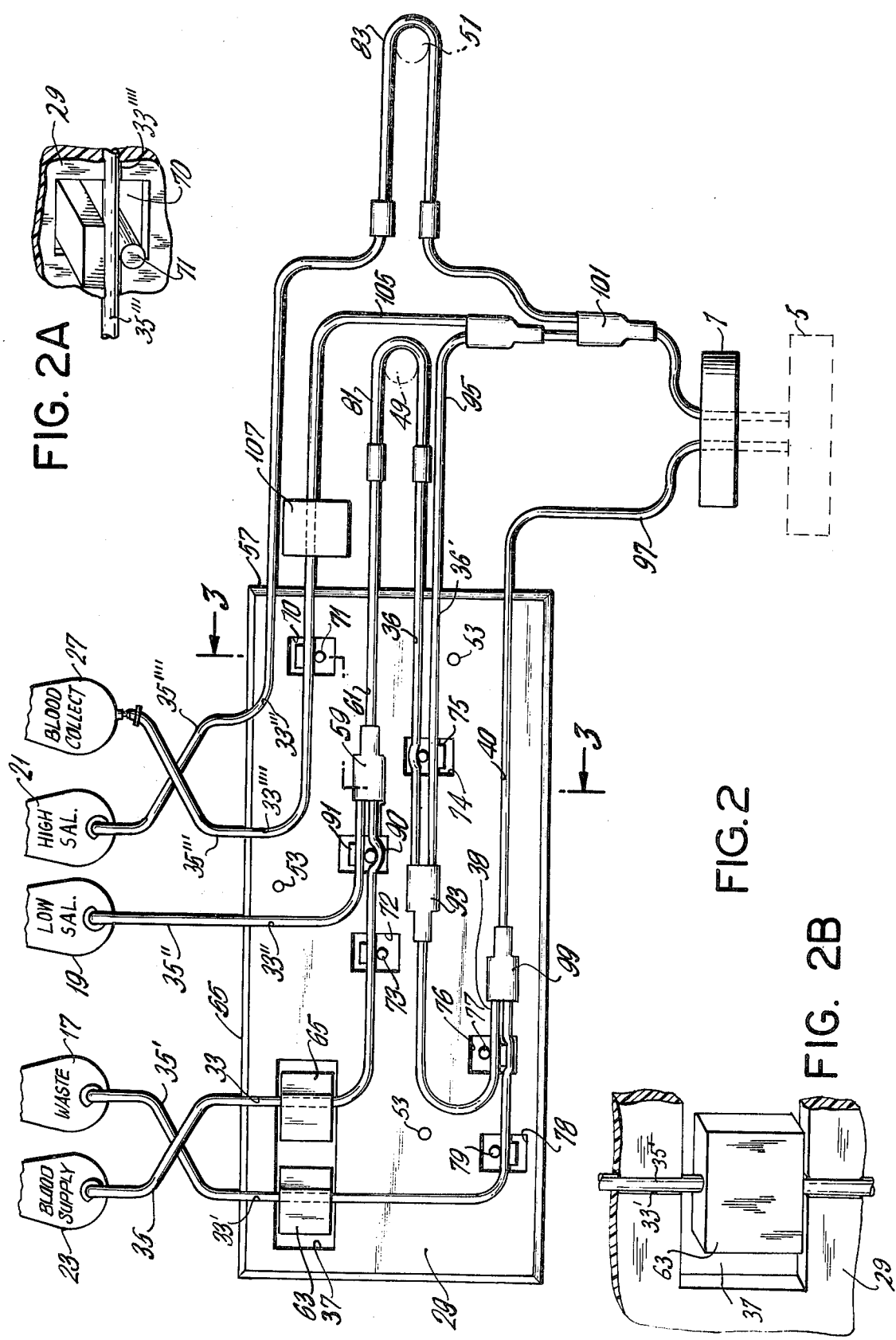

With reference to FIGS. 2, 3 and 4 packages 17, 19, 21, 23 and 27 are connected to flexible tubes 35-35'''', for example by means of a "Spike" connector arrangement as shown in FIG. 5 comprising a pointed extension member 22 which is force fitted by hand in conduit extension 26 and pierces a plastic membrane 30.

Board-like member 29 is mounted on pin arrangement 31 on housing 3 by means of holes 53 in board-like member 29. Each of the flexible conduits 35-35'''' is forced fitted into a groove 33-33'''' which extends from the upper edge 55 of board-like member 29 to the side 57 of board-like member 29 which is adjacent the horizontally disposed peristaltic pump shafts 49 and 51 as shown in FIG. 1. An additional groove 36 extends from side 57 into the interior of board-like member 29 to join with groove 33' at 38 into a single groove 40. A further additional groove 39 extends parallel to groove 36 and joins groove 36 at 94. As shown in FIG. 2, grooves 33 and 33'' join at 59 into a single groove 61. Board-like member 29 is provided with openings at locations along various groove paths to accommodate optical sensors 63 and 65, in opening 37, and pinch valves 71, 73, 75, 77, 79 and 91 in openings 70, 72, 74, 76, 78 and 90 respectively. The above noted optical sensors and pinch valves are mounted on housing 3 and are electrically connected to control unit 43 as shown in FIG. 1.

With the flexible tubes 35-35'''' assembled in board-like member 29 and the tubes connected to packages 17, 19, 21, 23 and 27 as shown in FIG. 1, loops 81 and 83 are fitted around peristaltic pumps shafts 49 and 51 as also shown in FIG. 1 and held fixed with respect to the shafts by clamps 85 and 87 as shown in FIG. 1.

With the tube harness arrangement of the present invention in place as described above, the blood washing apparatus shown in FIG. 1 can be operated. For example, low concentration saline solution from package 19 is pumped by the rotation of peristaltic pump shaft 49 through tube 35" to T connection 59, valve 91 being open, to T connection 93 where flow is reversed, due to valve 77 being closed and valve 75 being open, whereby low concentration saline solution passes through tube section 95 via connector 7 into rotating enclosure member 5, thereby priming enclosure member 5. Low saline solution in excess of that required for priming exits enclosure member 5 via connector 7 and tube section 97 through T connection 99 and tube 35' to waste package 17. After priming with low concentration saline solution valve 73 is opened and, blood from package 23 is pumped via tube 35 into enclosure member 5 by the same path as previously described low concentration saline solution prime. Optical sensor 65 detects the start and finish of blood flow through transparent tube 35 and at the finish provide an electrical signal to control unit 43, shown in FIG. 1, so that signals can be provided to the valves and pumps in the following "wash" step.

In the "wash" step, pump shafts 49 and 51 can be both operated to provide a continuous flow of saline solution of predetermined relatively high concentration into enclosure member 5, the higher saline concentration solution proceeding directly from package 21 via flexible tube 35"" through T connecton 101 and connector 7 to enclosure member 5; the low concentration saline solution proceeds from package 19 in the same manner as the above described priming step. During the washing step, saline solution containing contaminants, etc., i.e. waste liquid is continuously removed from enclosure member 5 to waste package 17 in the same manner as excess saline solution was removed in the above described priming step. When the predetermined washing period is over, the washed blood is collected from enclosure member 5 into package 27 by centrifugal force and the action of pump shaft 49 which pumps low concentration saline solution from package 19 into enclosure member 5 by way of tube 35", open valve 91 T connection 59, tubes 81 and 36, T connection 93, open valve 77, T connection 99 and tube 97. The washed blood exits through T connection 101 tube 105, open valve 71 and tube 35''' to blood collecton package 27. During the foregoing collection step valves 79 and 75 are closed and pump 51 is deactuated. The passage of washed blood is detected by optical sensor 107 and when blood is no longer detected the pump shaft 49 is stopped by a signal from control unit 43. Optical sensor 63 monitors the flow of waste liquid into waste collection package 17.

What is claimed is:

1. In combination with a blood washing apparatus having a (i) a housing member supporting a horizontal array of packages adapted to contain blood, saline solution and blood washing waste liquid (ii) a pair of adjacent peristaltic pump shafts located below and to the side of said array of packages (iii) a rotatable enclosure member arranged below said array of packages adapted to receive blood and saline solution from selected packages of said array and adapted to provide washed blood and waste liquid for transmission to selected packages of said array, a tubing harness arrangement for providing fluid paths between the packages of said array and said rotatable enclosure comprising a. a board-like member removably vertically mounted on said housing member below said array of packages and adjacent said pair of peristaltic pump shafts in a common plane with a cross-section of said shafts, said board-like member having a plurality of grooves extending from its upper horizontal side adjacent said array of package to a vertical side adjacent said pair of peristaltic pump shafts and an additional groove extending from said vertical side to a selected one of said plurality of grooves, a plurality of flexible tube members engaged in said grooves and respectively connected to a selected package of said array adjacent the upper side of said board-like member and providing fluid paths from said array of packages to said rotatable enclosure member, two of said plurality of flexible tube members being formed in a loop adjacent said vertical side of said board-like member which are respectively engaged to a said peristaltic pump shaft, the flexible tube member of one of said loops being doubled back to engage in said additional groove in saidboard-like member to firmly engage said board-like member to said peristaltic pump shaft.

2. A combination in accordance with claim 1 wherein said flexible tubes are transparent.

* * * * *